United States Patent
Wang et al.

(10) Patent No.: US 12,423,814 B2
(45) Date of Patent: Sep. 23, 2025

(54) METHODS, DEVICES, AND APPARATUSES FOR TESTING IMAGING QUALITY FOR NYSTAGMUS PATIENTS

(71) Applicant: Chaomu Technology (Beijing) Co., Ltd., Beijing (CN)

(72) Inventors: Lejin Wang, Beijing (CN); Wensi Wang, Beijing (CN); Zhen Xiao, Beijing (CN); Tianfang Wang, Beijing (CN); Duo Wang, Beijing (CN)

(73) Assignee: Chaomu Technology (Beijing) Co., Ltd., Beijing (CN)

( * ) Notice: Subject to any disclaimer, the term of this patent is extended or adjusted under 35 U.S.C. 154(b) by 0 days.

(21) Appl. No.: 18/930,446

(22) Filed: Oct. 29, 2024

(65) Prior Publication Data
US 2025/0124574 A1 Apr. 17, 2025

Related U.S. Application Data

(63) Continuation of application No. PCT/CN2024/124116, filed on Oct. 11, 2024.

(30) Foreign Application Priority Data

Oct. 12, 2023 (CN) .......................... 202311317634.5

(51) Int. Cl.
*G06T 7/00* (2017.01)
*A61B 3/113* (2006.01)

(52) U.S. Cl.
CPC ............ *G06T 7/0012* (2013.01); *A61B 3/113* (2013.01); *G06T 2207/20081* (2013.01); *G06T 2207/30041* (2013.01); *G06T 2207/30168* (2013.01)

(58) Field of Classification Search
CPC ......... G06T 7/0012; G06T 2207/20081; G06T 2207/30041; G06T 2207/30168; A61B 3/113
USPC .......................................................... 351/209
See application file for complete search history.

(56) References Cited

U.S. PATENT DOCUMENTS

| | | | |
|---|---|---|---|
| 8,820,931 B2 * | 9/2014 | Walsh | A61B 3/0025 351/208 |
| 9,492,079 B2 * | 11/2016 | Walsh | A61B 3/113 |
| 12,254,737 B2 * | 3/2025 | Shigeta | G06F 18/217 |
| 2015/0085253 A1 * | 3/2015 | Walsh | A61B 3/18 351/208 |
| 2021/0386285 A1 * | 12/2021 | Walsh | A61B 3/102 |

FOREIGN PATENT DOCUMENTS

| | | |
|---|---|---|
| CN | 113662822 A | 11/2021 |
| CN | 114782394 A | 7/2022 |
| CN | 115590462 A | 1/2023 |

(Continued)

OTHER PUBLICATIONS

"Dynamic Prediction of Psychological Therapy Effectiveness Model," Xiaoxin Psychology Jan. 22, 2022 15:12, https://www.sohu.com/a/518357798_120014135 (6 pages).

(Continued)

*Primary Examiner* — Mohammed A Hasan
(74) *Attorney, Agent, or Firm* — Jones Day

(57) ABSTRACT

The present disclosure relates to medical imaging testing, and specifically to methods, devices, and apparatuses for testing imaging quality for nystagmus patients.

26 Claims, 3 Drawing Sheets

(56) References Cited

FOREIGN PATENT DOCUMENTS

| CN | 116392370 A | * | 7/2023 |
| CN | 117058148 A | * | 11/2023 |
| CN | 117058148 B | | 2/2024 |
| KR | 20210140808 A | | 11/2021 |

OTHER PUBLICATIONS

First Office Action and Notice, Chinese Patent Application No. CN202311317634.5 (Pub No. CN117058148A) mailed Nov. 17, 2023 (19 pages).
Hong Yang, 2012, "Quantitative diagnosis and pathogenesis of congenital idiopathic nystagmus," Nov. 15, 2012 (114 pages).
Notification of Preliminary Examination Qualification for Invention Patent Application, Chinese Patent Application No. CN202311317634.5 (Pub No. CN117058148A) mailed Oct. 25, 2023 (2 pages).
International Searching Authority, International Search Report and Written Opinion for International Patent Application No. PCT/CN2024/124116 mailed Dec. 11, 2024 (10 pages).

* cited by examiner

METHODS, DEVICES, AND APPARATUSES FOR TESTING IMAGING QUALITY FOR NYSTAGMUS PATIENTS

CROSS-REFERENCE TO RELATED APPLICATIONS

This application is a continuation of International Patent Application No. PCT/CN2024/124116, filed Oct. 11, 2024, which claims priority to Chinese Patent Application No. 202311317634.5, filed Oct. 12, 2023, granted as CN 117058148 B on Feb. 2, 2024, the contents of each of which are incorporated by reference in their entireties herein, and to each of which priority is claimed.

1. TECHNICAL FIELD

The present disclosure relates to medical imaging testing, and specifically to methods, devices, and apparatuses for testing imaging quality for nystagmus patients.

2. BACKGROUND

Nystagmus patients are different from general myopia patients who can achieve improved vision by correction through glasses. This is because nystagmus cannot be corrected by glasses, and is generally treated by operations and/or surgeries. In contrast to those conditions that may be conveniently treated with glasses, it is difficult to predict the postoperative vision level of nystagmus patients after operations. Furthermore, in addition to nystagmus, there may be other eye diseases affecting the vision or other factors causing hypoplasia. However, the current testing methods are mainly for a stable visual target, but cannot accurately evaluate the imaging quality. Though the eye movement tracking device can capture the data of nystagmus, it is still necessary for the surgeons to participate the determination and evaluation of the eye symptoms of the patients. Currently, there is no effective preoperative evaluation tool, and thus surgeons cannot predict the postoperative visual correction effects of the patients quickly and accurately.

3. SUMMARY

The present disclosure provides apparatuses and methods for testing imaging quality of eyeballs of nystagmus patients, which can solve the problems in the art: that the postoperative imaging quality of the eyeballs of the nystagmus patients cannot be accurately evaluated before operations and/or surgeries.

In a first aspect of the present disclosure, a method for testing imaging quality for a nystagmus patient is provided, wherein the method comprises: obtaining preoperative movement data of an eyeball of a nystagmus patient in real time; adjusting a position of a visual target according to the preoperative movement data such that the adjusted position of the visual target is consistent with a sight direction in the preoperative movement data; evaluating the imaging quality for the nystagmus patient, according to a vision imaging result when the sight direction is consistent with the position of the visual target, to obtain an evaluation result; and predicting a postoperative result of the nystagmus patient according to the evaluation result and a pre-trained treatment evaluation model.

In certain embodiments of the method disclosed herein, by obtaining preoperative movement data of the nystagmus patient in real time, it is possible to record the movement information of the eyeball of the patient accurately, providing an accurate data basis for the subsequent analysis and adjustment. By adjusting a position of a visual target according to the preoperative movement data, it is possible to ensure that the sight line of the eyeball of the patient is kept consistent with the visual target, better sensing the movement of the eyeball of the patient. By a manner of predicting a postoperative result of the nystagmus patient based on the evaluation result and a pre-trained treatment evaluation model, the quality of the eye of the nystagmus patient after operation is predicted, thus providing accurate evaluation for the postoperative effect and helping the surgeon and the patient to understand the effect and progress of the operation treatment for the nystagmus.

In certain embodiments of the method disclosed herein, the step of adjusting the position of the visual target according to the preoperative movement data comprises: obtaining preoperative historical movement data of the eyeball of the nystagmus patient; using the historical movement data to build an eye movement prediction model; predicting movement data of the eyeball at the next moment according to the eye movement prediction model and the movement data of the eyeball at the current moment; and adjusting the position of the visual target according to the sight direction determined by the predicted movement data of the eyeball at the next moment.

By predicting the movement data of the eyeball at the next moment in real time and accordingly adjusting the visual target, it is possible to provide fast feedback and adjustment during practical imaging, thus ensuring the imaging quality in real time, and in turn ensuring the accuracy of the postoperative result of the nystagmus patient as predicted later according to the evaluation result and a pre-trained treatment evaluation model.

In certain embodiments of the method disclosed herein, the step of using the historical movement data to build the eye movement prediction model comprises: performing fitting analysis for the historical movement data based on the anatomical and physiological principles to build the eye movement prediction model; or, using the historical movement data to train an autoencoder to build the eye movement prediction model.

By performing fitting analysis for the historical movement data based on the anatomical and physiological principles, it is possible to better understand the biological mechanism of the nystagmus. By using the historical movement data to train an autoencoder, it is possible for the model to learn the special movement mode(s) of the nystagmus of the patient, including speed, amplitude, direction, and so on. Either of the two manners can build the model according to the historical movement data of each patient, facilitating building a more precise eye movement prediction model and thus predicting the movement track of the eyeball more accurately.

In certain embodiments of the method disclosed herein, the step of adjusting the position of the visual target according to the preoperative movement data comprises: obtaining preoperative historical movement data of the eyeball of the nystagmus patient; using the historical movement data to train a machine learning model to obtain a nystagmus identification model for identifying a speed and an amplitude of the nystagmus; inputting the movement data as obtained in real time into the nystagmus identification model to obtain the current speed and amplitude of the nystagmus; and adjusting the position of the visual target according to the current speed and amplitude of the nystagmus.

By training the nystagmus identification model to identify the speed and amplitude of the nystagmus, it is possible to capture the features of the nystagmus of the patient more accurately. After the movement data as obtained in real time are input into the nystagmus identification model, it is possible to obtain the current speed and amplitude of the nystagmus more precisely, thus improving the precision of adjustment of the visual target.

In certain embodiments of the method disclosed herein, after the step of obtaining the preoperative movement data of the eyeball of the nystagmus patient in real time, the method further comprises: performing filtering processing to the preoperative movement data according to an adaptive filtering algorithm.

By the filtering processing, it is possible to facilitate reducing noise, smoothing the movement track, and decreasing error, thus improving the reliability and accuracy of the method for testing imaging quality for the nystagmus patient.

In certain embodiments of the method disclosed herein, the step of predicting the postoperative result of the nystagmus patient according to the evaluation result and the pre-trained treatment evaluation model comprises: obtaining a historical evaluation result of the eyeball of the nystagmus patient and a corresponding treatment result; using the historical evaluation result and the corresponding treatment result to train the machine learning model to obtain the treatment evaluation model; and inputting the evaluation result into the treatment evaluation model to determine the postoperative result of the nystagmus patient.

By using the historical evaluation result(s) and the treatment result, it is possible to provide personalized treatment evaluation for each patient. The treatment evaluation model can predict the postoperative effect of the patient after treatment, including the improvement in symptom and the change in vision, facilitating the surgeon and the patient to understand the nystagmus operation treatment effect and progress.

In certain embodiments of the method disclosed herein, the evaluation result comprises visual clarity, contrast, and stability.

In a second aspect of the present disclosure, a device for testing imaging quality for a nystagmus patient is provided, comprising: a data obtaining module, for obtaining movement data of an eyeball of the nystagmus patient in real time; an adjusting module, for adjusting a position of a visual target according to the movement data such that the adjusted position of the visual target is consistent with a sight direction in the movement data; an evaluation module, for evaluating the imaging quality for the nystagmus patient, according to a vision imaging result when the sight direction is consistent with the position of the visual target, to obtain an evaluation result; and a prediction module, for predicting a treatment result of the nystagmus patient according to the evaluation result and a pre-trained treatment evaluation model.

In certain embodiments of the device disclosed herein, adjusting the position of the visual target according to the preoperative movement data comprises: obtaining preoperative historical movement data of the eyeball of the nystagmus patient; using the historical movement data to build an eye movement prediction model; predicting movement data of the eyeball at the next moment according to the eye movement prediction model and the movement data of the eyeball at the current moment; and adjusting the position of the visual target according to the sight direction determined by the movement data of the eyeball at the next moment.

In certain embodiments of the device disclosed herein, using the historical movement data to build the eye movement prediction model comprises: performing fitting analysis for the historical movement data based on the anatomical and physiological principles to build the eye movement prediction model; or using the historical movement data to train an autoencoder to build the eye movement prediction model.

In certain embodiments of the device disclosed herein, adjusting the position of the visual target according to the preoperative movement data comprises: obtaining preoperative historical movement data of the eyeball of the nystagmus patient; using the historical movement data to train a machine learning model to obtain a nystagmus identification model for identifying a speed and an amplitude of the nystagmus; inputting the movement data as obtained in real time into the nystagmus identification model to obtain the current speed and amplitude of the nystagmus; and adjusting the position of the visual target according to the current speed and amplitude of the nystagmus.

In certain embodiments of the device disclosed herein, the device disclosed herein further comprises a filtration module, for performing filtering processing to the preoperative movement data according to an adaptive filtering algorithm.

In certain embodiments of the device disclosed herein, predicting the postoperative result of the nystagmus patient according to the evaluation result and the pre-trained treatment evaluation model comprises: obtaining a historical evaluation result of the eyeball of the nystagmus patient and a corresponding treatment result; using the historical evaluation result and the corresponding treatment result to train the machine learning model to obtain the treatment evaluation model; and inputting the evaluation result into the treatment evaluation model to determine the postoperative result of the nystagmus patient.

In certain embodiments of the device disclosed herein, the evaluation result comprises visual clarity, contrast, and stability.

In a third aspect of the present disclosure, an apparatus for testing imaging quality for a nystagmus patient is provided, comprising: a display, for displaying a visual target; an eye movement tracking system, for tracking movement of an eyeball of the nystagmus patient in real time to obtain movement data; and a processor, for adjusting a position of a visual target according to the movement data such that the adjusted position of the visual target is consistent with a sight direction in the movement data; evaluating the imaging quality for the nystagmus patient, according to a vision imaging result when the sight direction is consistent with the position of the visual target, to obtain an evaluation result; and predicting a treatment result of the nystagmus patient according to the evaluation result and a pre-trained treatment evaluation model.

In certain embodiments of the apparatus disclosed herein, adjusting the position of the visual target according to the preoperative movement data comprises: obtaining preoperative historical movement data of the eyeball of the nystagmus patient; using the historical movement data to build an eye movement prediction model; predicting movement data of the eyeball at the next moment according to the eye movement prediction model and the movement data of the eyeball at the current moment; and adjusting the position of the visual target according to the sight direction determined by the movement data of the eyeball at the next moment.

In certain embodiments of the apparatus disclosed herein, adjusting the position of the visual target according to the preoperative movement data comprises: obtaining preoperative historical movement data of the eyeball of the nystagmus patient; using the historical movement data to train a machine learning model to obtain a nystagmus identification model for identifying a speed and an amplitude of the nystagmus; inputting the movement data as obtained in real time into the nystagmus identification model to obtain the current speed and amplitude of the nystagmus; and adjusting the position of the visual target according to the current speed and amplitude of the nystagmus.

In certain embodiments of the apparatus disclosed herein, using the historical movement data to build the eye movement prediction model comprises: performing fitting analysis for the historical movement data based on the anatomical and physiological principles to build the eye movement prediction model; or using the historical movement data to train an autoencoder to build the eye movement prediction model.

In certain embodiments of the apparatus disclosed herein, predicting the postoperative result of the nystagmus patient according to the evaluation result and the pre-trained treatment evaluation model comprises: obtaining a historical evaluation result of the eyeball of the nystagmus patient and a corresponding treatment result; using the historical evaluation result and the corresponding treatment result to train the machine learning model to obtain the treatment evaluation model; and inputting the evaluation result into the treatment evaluation model to determine the postoperative result of the nystagmus patient.

In certain embodiments of the apparatus disclosed herein, the eye movement tracking device is also configured to perform filtering processing to the preoperative movement data according to an adaptive filtering algorithm In certain embodiments of the apparatus disclosed herein, the evaluation result comprises visual clarity, contrast, and stability.

In certain embodiments of the apparatus disclosed herein, by the combination of the display and the eye movement tracking device, the movement of the eyeball of the nystagmus patient is tracked, and it is possible to provide the accurate and clear display for the movement of the visual target such that the nystagmus patient can better sense the movement of his/her eyeball. Moreover, with the device for testing, by the functions of visual target prediction and matching, it is possible to maintain synchronization of the visual target with respect to the movement of the eyeball, improving the accuracy and stability of the visual target. By the function of quality evaluation, it is possible to provide the evaluation for the postoperative effect, helping the surgeon and the patient to understand the nystagmus operation effect and progress.

In a fourth aspect of the present disclosure, a computer apparatus is provided, comprising: a memory and a processor which are in communication with each other, wherein the memory is stored therein with a computer instruction, and when the computer instruction is executed by the processor, the method for testing imaging quality for the nystagmus patient according to the above first aspect or any embodiments corresponding thereto is implemented.

In a fifth aspect of the present disclosure, a computer-readable storage medium is provided, and it is stored thereon with a computer instruction which is used to make a computer implement the method for testing imaging quality for the nystagmus patient according to the above first aspect or any embodiments corresponding thereto.

4. BRIEF DESCRIPTION OF THE FIGURES

In order to explain the technical solutions in the specific embodiments of the present invention or in the prior art more clearly, the figures necessary to be used in the description for the specific embodiments or the prior art is briefly introduced hereinafter. Apparently, the figures used in the following description are for some embodiments of the present disclosure. Based on these figures, it is possible for those skilled in the art to obtain other figures, without any inventive work.

5. DETAILED DESCRIPTION

Hereinafter, the technical solutions of the present invention are described clearly and completely in connection with the figures. Apparently, the described embodiments are some embodiments in the present invention, rather than all embodiments. Any other embodiments obtained based on the embodiments in the present invention by those skilled in the art without any inventive work fall within the protection scope of the present disclosure.

The related technical features in different embodiments of the present disclosure as described below can be combined with one another as long as there is no contradiction therebetween.

In one aspect, the present disclosure provides methods for testing imaging quality for nystagmus patients. It should be noted that the steps as shown in the flow chart of the figures can be executed in a computer system, such as a group of computer-executable instructions. Moreover, though a logic sequence is shown in the flow charts, the steps as shown or described can be executed in a different sequence in some circumstances.

Figure 1:
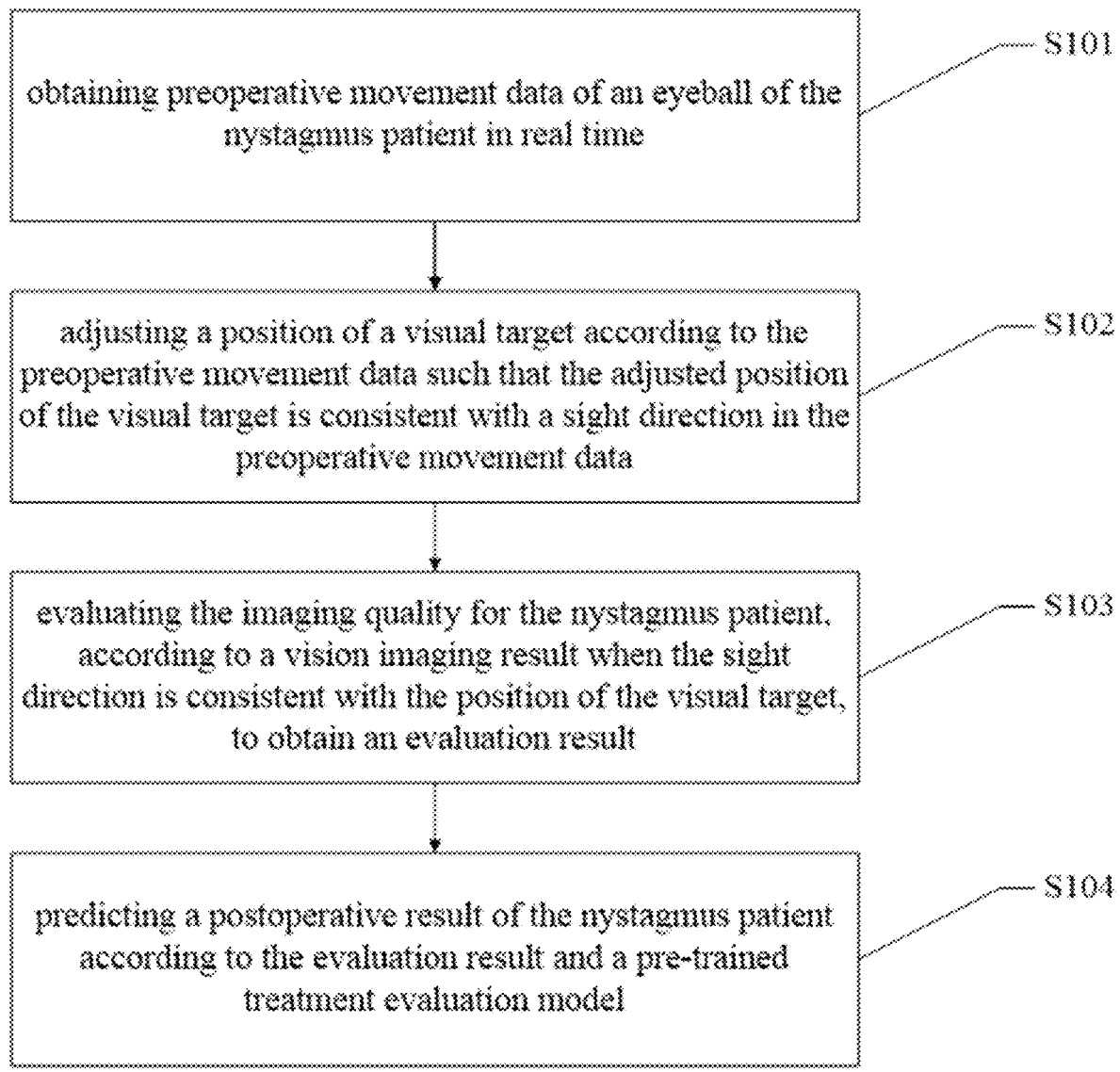
FIG. 1 is a flow chart of a method for testing imaging quality for an eyeball of a nystagmus patient according to an exemplary embodiment of the present disclosure.

In certain embodiments, a method for testing imaging quality for a nystagmus patient is provided, which can be used in the above-described computer apparatus. FIG. 1 is a flow chart of a method for testing imaging quality for a nystagmus patient according to an exemplary embodiment of the present disclosure. As shown in FIG. 1, the flow chart comprises the steps as follows:

Step S101: obtaining preoperative movement data of an eyeball of a nystagmus patient in real time.

It should be noted that nystagmus is a dysfunction of eye movement. The patient exhibits unwilling and irregular fast eyeball movement. Such a symptom makes the visual sense become difficult because the eyeball can not maintain a stable focus. As used herein, the term "nystagmus" refers to the abnormal movement of an eye of a patient, which can cause the vision to be obscured or unstable. As used herein, the term "preoperative movement data" refers to the information related to the movement of the eyeball of the patient collected before the eye operation/surgery or treatment. In certain embodiments, the preoperative movement data comprises a position, a speed, and/or an acceleration of the eyeball, and can be used for analyzing and evaluating the movement mode and feature(s) of the eyeball of the patient.

In certain embodiments, there is no limitation as to the specifically obtained preoperative movement data.

Step S102: adjusting a position of a visual target according to the preoperative movement data such that the adjusted position of the visual target is consistent with a sight direction in the preoperative movement data.

It should be noted that the visual target can be a certain pattern, text or label displayed on the screen, and it is necessary for the patient to pay visual attention thereto. In certain embodiments, the visual target is used to guide the movement of the eyeball of the patient. That is, the sight direction of the eyeball is kept consistent with the position of the visual target to facilitate the later measurement and evaluation of the visual imaging quality thereof. The visual target can be the visual target in the general visual testing chart (such as the international standard log visual testing chart), the visual target in the Snellen visual testing chart, or the visual target in the EDTRs (Early Treatment Diabetic Retinopathy Study visual testing chart), or it can be a stripe visual target for measuring the contrast sensitivity. Thus, not only can the vision of the patient be measured, but also the contrast sensitivity of the patient can be measured, obtaining a more accurate visual quality evaluation result.

Step S103: evaluating the imaging quality for the nystagmus patient, according to a vision imaging result when the sight direction is consistent with the position of the visual target, to obtain an evaluation result.

In certain embodiments, the step of evaluating the imaging quality is a process of quantitatively evaluating the visual imaging quality of the patient, to determine the visual quality of the nystagmus patient. The evaluation result can be a value or an index obtained during the evaluation, for describing the visual condition of the patient. The evaluation result can comprise the visual clarity, contrast and/or stability, and/or other information.

Step S104: predicting a postoperative result of the nystagmus patient according to the evaluation result and a pre-trained treatment evaluation model.

It should be noted that the pre-trained treatment evaluation model can be a machine learning model which can use the preoperative movement data, the imaging quality evaluation result and other information for training, and can be used for predicting a visual result of the patient after treatment or operation. As used herein, the postoperative (after operation/surgery) result is the evaluation of the vision or visual imaging quality of the patient after treatment or operation, and can be helpful for the surgeon and the patient to understand the operation treatment effect and progress. The data used for model building can comprise not only the parameters of the nystagmus, but also other parameters of eye diseases affecting the vision.

In certain embodiments, by obtaining preoperative movement data of the nystagmus patient in real time, it is possible to record the movement information of the eyeball of the patient accurately, providing an accurate data basis for the subsequent analysis and adjustment. By adjusting a position of a visual target according to the preoperative movement data, it is possible to ensure that the sight line of the eyeball of the patient is kept consistent with the visual target, better sensing the movement of the eyeball of the patient. By a manner of predicting a postoperative result of the nystagmus patient based on the evaluation result and a pre-trained treatment evaluation model, the quality of the eye of the nystagmus patient after operation is predicted, thus providing accurate evaluation for the postoperative effect, and helping the surgeon and the patient to understand the effect and progress of the operation treatment for the nystagmus.

In certain embodiments, a method for testing imaging quality for a nystagmus patient is further provided, and the flow chart comprises the following steps:

Step S201: obtaining preoperative movement data of an eyeball of the nystagmus patient in real time. Please refer to Step S101 in the exemplary embodiment as shown in FIG. 1 for details, which are not repeated herein.

Specifically, the above-described Step S201 comprises:

S2011: obtaining preoperative historical movement data of the eyeball of the nystagmus patient.

It should be noted that the historical movement data refer to the data related to the eye movement of the nystagmus patient within a period of time before operation/surgery, including the position, speed, acceleration, moving track and the like of the eyeball, which are not limited to the embodiments of the present disclosure.

S2012: using the historical movement data to build an eye movement prediction model. Specifically, the step comprises: performing fitting analysis for the historical movement data based on the anatomical and physiological principles to build the eye movement prediction model; or, using the historical movement data to train an autoencoder to build the eye movement prediction model.

In certain embodiments, to perform fitting analysis for the historical movement data of the nystagmus patient by means of the anatomical and physiological principles. For example, it is possible to analyze the movement mode of the nystagmus according to the anatomical structure and the physiology characteristics of the eyeball, thus building a model which can predict the movement of the eyeball in the future. The autoencoder can be a neural network model, for learning compressive expression of data. In certain embodiments, the autoencoder is used to train the historical movement data of the nystagmus patient, thus building the eye movement prediction model. The autoencoder learns useful features from the data and then uses these features to predict the movement of the eyeball in the future. Either of the two manners can build the model according to the historical movement data of each patient, facilitating building a more precise eye movement prediction model and thus predicting the movement track of the eyeball more accurately.

S2013: predicting movement data of the eyeball at the next moment according to the eye movement prediction model and the movement data of the eyeball at the current moment.

Specifically, it is possible to input the movement data of the eyeball at the current moment into the eye movement prediction model, and thus it is possible to predict and obtain the movement data of the eyeball at the next moment. For example, the position of the eyeball at the current moment is input into the eye movement prediction model, and by means of the eyeball movement pattern learned by the eye movement prediction model, a position of the eyeball at the next moment is predicted. Herein, the movement data of the eyeball at the next moment are predicted such that the position of the visual target can be adjusted in real time to make it match the movement of the eyeball. Thus, it is possible to improve the vision imaging quality such that the nystagmus patient can see the visual target more clearly and more accurately.

S2014: adjusting the position of the visual target according to the sight direction determined by the movement data of the eyeball at the next moment.

Hereinafter, an example of building the model by the autoencoder is provided herein. Before a preset moment T0, the data of the position of the eyeball in the sight direction are collected. In the data at the moment T0, the input portion is X=(T0−1, T0−2, T0−3 . . . . T0-*t*), i.e., a group of eyeball position data at the past moments. The eyeball position data collected before the moment T0 are used as the input and the eyeball position data at the moment T0 are used as the output, building a training set. The output portion is the eyeball position at the moment of Y=T0, also a group of data, such as Y=(T0+1, T0+2 . . . ). The training set is used to train a deep neutral network autoencoder f. The above two groups of data are used to train the autoencoder wherein the input layer dimension of the autoencoder is the dimension of the data of the position of the eyeball in the past, and the output layer dimension thereof is the dimension of the data of the position of the eyeball at the current moment. During the training, the model learns the feature expression by a manner of automatically encoding and decoding the data. Based on the autoencoder f, the eyeball position data at the past moment(s) X are input thereto and a predicted eyeball position f (X) is generated, and the visual target is adjusted to the eyeball position f (X) on the display screen. By the trained autoencoder model f, when the eyeball position data X at the past moment(s) are input, a predicted result of the eyeball position f (X) at the current moment can be generated. It is necessary to be noted that during the training, it is possible to adjust the parameter(s) of the autoencoder to minimize $|f(X)-Y|^2$ such that the trained autoencoder can accurately predict the movement data at the next moment according to the movement data at the current moment. Finally, according to the predicted eyeball position, the position of the visual target is adjusted on the display screen such that it is consistent with the predicted eyeball position.

In certain embodiments, the above methods use the movement data of the eyeball within a period of time in the past to predict a direction of movement of the eyeball in a relatively short range of time in the future. For example, within 1 second, a direction of movement of the eyeball in the next 0.1 second is predicted. The position of the visual target is adjusted in advance, reducing delay of the position of the visual target with respect to the current position of the eyeball.

Step S202: adjusting a position of a visual target according to the preoperative movement data such that the adjusted position of the visual target is consistent with a sight direction in the preoperative movement data. Please refer to Step S102 in the exemplary embodiment as shown in FIG. 1 for details, which are not repeated herein.

Step S203: evaluating the imaging quality for the nystagmus patient, according to a vision imaging result when the sight direction is consistent with the position of the visual target, to obtain an evaluation result. Please refer to Step S103 in the embodiment as shown in FIG. 1 for details, which are not repeated herein.

Step S204: predicting a postoperative result of the nystagmus patient according to the evaluation result and a pre-trained treatment evaluation model. Please refer to Step S104 in the exemplary embodiment as shown in FIG. 1 for details, which are not repeated herein.

In certain embodiments, by predicting the movement data of the eyeball at the next moment in real time and accordingly adjusting the visual target, it is possible to provide fast feedback and adjustment during practical imaging, thus ensuring the imaging quality in real time, and in turn ensuring the accuracy of the postoperative result of the nystagmus patient as predicted later according to the evaluation result and a pre-trained treatment evaluation model.

In certain embodiments, a method for testing imaging quality for a nystagmus patient is further provided, and the flow chart comprises the following steps:

Step S301: obtaining preoperative movement data of an eyeball of the nystagmus patient in real time. In certain embodiments, the Step S301 further comprises:

S3011: obtaining preoperative historical movement data of the eyeball of the nystagmus patient.

S3012: using the historical movement data to train a machine learning model to obtain a nystagmus identification model for identifying a speed and an amplitude of the nystagmus.

Specifically, it is possible to train the machine learning model, such as a support vector machine or a neural network, to obtain the nystagmus identification model. The purpose of training is to enable the model to automatically identify the speed and amplitude of the nystagmus. During the training, the historical movement data are used as the input, and the corresponding speed and amplitude of the nystagmus are used as the output, for training the model. By multiple times of iteration and optimization, the model gradually learns how to extract useful features from the input data and predict the speed and amplitude of the nystagmus accurately.

S3013: inputting the movement data as obtained in real time into the nystagmus identification model to obtain the current speed and amplitude of the nystagmus.

S3014: adjusting the position of the visual target according to the current speed and amplitude of the nystagmus.

Step S302: adjusting a position of a visual target according to the preoperative movement data such that the adjusted position of the visual target is consistent with a sight direction in the preoperative movement data. Please refer to Step S102 in the exemplary embodiment as shown in FIG. 1 for details, which are not repeated herein.

Step S303: evaluating the imaging quality for the nystagmus patient, according to a vision imaging result when the sight direction is consistent with the position of the visual target, to obtain an evaluation result. Please refer to Step S103 in the exemplary embodiment as shown in FIG. 1 for details, which are not repeated herein.

Step S304: predicting a postoperative result of the nystagmus patient according to the evaluation result and a pre-trained treatment evaluation model. Please refer to Step S104 in the exemplary embodiment as shown in FIG. 1 for details, which are not repeated herein.

In certain embodiments, by training the nystagmus identification model to identify the speed and amplitude of the nystagmus, it is possible to capture the features of the nystagmus of the patient more accurately. After the movement data as obtained in real time are input into the nystagmus identification model, it is possible to obtain the current speed and amplitude of the nystagmus more precisely, thus improving the precision of adjustment of the visual target.

In certain embodiments, a method for testing imaging quality for a nystagmus patient is further provided, and the flow chart comprises the following steps:

Step S401: obtaining preoperative movement data of an eyeball of the nystagmus patient in real time. Please refer to Step S101 in the exemplary embodiment as shown in FIG. 1 for details, which are not repeated herein.

Step S402: performing filtering processing to the movement data according to an adaptive filtering algorithm.

By the filtering processing, it is possible to facilitate reducing noise, smoothing the movement track, and decreasing error, thus improving the reliability and accuracy of the method for testing imaging quality for the nystagmus patient.

Step S403: adjusting a position of a visual target according to the preoperative movement data such that the adjusted position of the visual target is consistent with a sight direction in the preoperative movement data. Please refer to Step S102 in the exemplary embodiment as shown in FIG. 1 for details, which are not repeated herein.

Step S404: evaluating the imaging quality for the nystagmus patient, according to a vision imaging result when the sight direction is consistent with the position of the visual target, to obtain an evaluation result. Please refer to Step S103 in the exemplary embodiment as shown in FIG. 1 for details which, which are not repeated herein.

Step S405: predicting a postoperative result of the nystagmus patient according to the evaluation result and a pre-trained treatment evaluation model.

In certain embodiments, the above-described Step S405 comprises:

Step S4051: obtaining a historical evaluation result of the eyeball of the nystagmus patient and a corresponding treatment result.

It should be noted that the historical evaluation result refers to a plurality of historical evaluation results obtained by several times of imaging quality evaluation for the patient, and the treatment result refers to a plurality of treatment effects corresponding to the plurality of evaluation results.

Step S4052: using the historical evaluation result and the corresponding treatment result to train the machine learning model to obtain the treatment evaluation model.

Step S4053: inputting the evaluation result into the treatment evaluation model to determine the postoperative result of the nystagmus patient.

The current evaluation result of the patient is input into the trained treatment evaluation model. The model can automatically analyze the input data and output a predicted postoperative result. The postoperative result refers to the treatment effect after operation/surgery, i.e., whether the nystagmus is successfully relieved or eliminated by the operation/surgery and whether the vision of the patient is improved. It is possible to show the postoperative result by a nystagmus degree, a vision value, or other indexes.

In certain embodiments, by using the historical evaluation result(s) and the treatment result, it is possible to provide personalized treatment evaluation for each patient. The treatment evaluation model can predict the postoperative effect of the patient after treatment, including the improvement in symptom and the change in vision, facilitating the surgeon and the patient to understand the nystagmus operation treatment effect and progress.

In certain embodiments, a device for testing imaging quality for a nystagmus patient is further provided. The device is used to implement the above-described embodiments and preferred solutions, and the content already described is not repeated herein. The term "module" as used herein can implement a combination of software and/or hardware having a pre-determined function. Though the device disclosed herein is preferably implemented by software, it is possible and conceivable to implement the device by hardware or by a combination of software and hardware.

Figure 2:
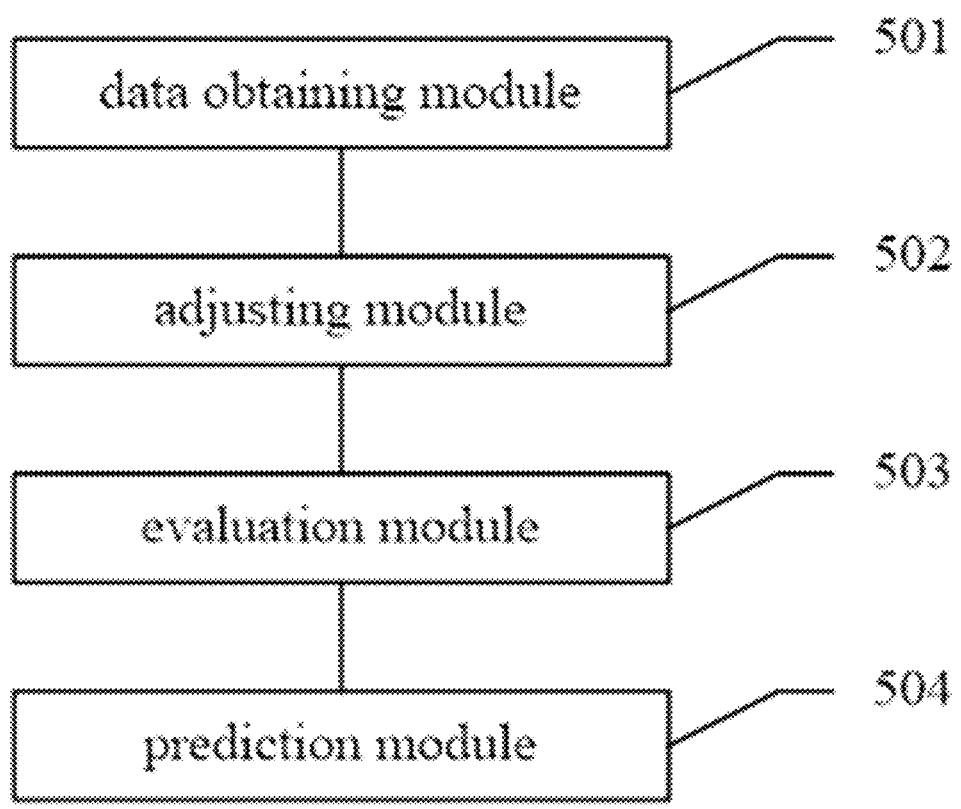
FIG. 2 is a diagram of component modules associated with a processor of a device for testing imaging quality for an eyeball of a nystagmus patient according to an exemplary embodiment of the present disclosure.

In certain embodiments, a device for testing imaging quality for a nystagmus patient is provided, and as shown in FIG. 2, it comprises: a data obtaining module 501, for obtaining preoperative movement data of an eyeball of the nystagmus patient in real time; an adjusting module 502, for adjusting a position of a visual target according to the preoperative movement data such that the adjusted position of the visual target is consistent with a sight direction in the preoperative movement data; an evaluation module 503, for evaluating the imaging quality for the nystagmus patient, according to a vision imaging result when the sight direction is consistent with the position of the visual target, to obtain an evaluation result; and a prediction module 504, for predicting a treatment result of the nystagmus patient according to the evaluation result and a pre-trained treatment evaluation model.

In certain embodiments, the adjusting module 502 is specifically used for obtaining preoperative historical movement data of the eyeball of the nystagmus patient; using the historical movement data to build an eye movement prediction model; predicting movement data of the eyeball at the next moment according to the eye movement prediction model and the movement data of the eyeball at the current moment; and adjusting the position of the visual target according to the sight direction determined by the movement data of the eyeball at the next moment.

In certain embodiments, the adjusting module 502 is specifically used for performing fitting analysis for the historical movement data based on the anatomical and physiological principles to build the eye movement prediction model; or, using the historical movement data to train an autoencoder to build the eye movement prediction model.

In certain embodiments, the adjusting module 502 is specifically used for obtaining preoperative historical movement data of the eyeball of the nystagmus patient; using the historical movement data to train a machine learning model to obtain a nystagmus identification model for identifying a speed and an amplitude of the nystagmus; inputting the movement data as obtained in real time into the nystagmus identification model to obtain the current speed and amplitude of the nystagmus; and adjusting the position of the visual target according to the current speed and amplitude of the nystagmus.

In certain embodiments, the device further comprises a filtering module, for performing filtering processing to the movement data according to an adaptive filtering algorithm.

In certain embodiments, the prediction module 504 is specifically used for obtaining a historical evaluation result of the eyeball of the nystagmus patient and a corresponding treatment result; using the historical evaluation result and the corresponding treatment result to train the machine learning model to obtain the treatment evaluation model; and inputting the evaluation result into the treatment evaluation model to determine the postoperative result of the nystagmus patient.

In certain embodiments, by obtaining the preoperative movement data of the nystagmus patient in real time, it is possible to record the movement information of the eyeball of the patient accurately, providing an accurate data basis for the subsequent analysis and adjustment. By adjusting a position of a visual target according to the preoperative movement data, it is possible to ensure that the sight line of the eyeball of the patient is kept consistent with the visual target, better sensing the movement of the eyeball of the patient. By a manner of predicting a postoperative result of the nystagmus patient based on the evaluation result and a pre-trained treatment evaluation model, the quality of the eye of the nystagmus patient after operation is predicted, thus providing accurate evaluation for the postoperative effect, and helping the surgeon and the patient to understand the effect and progress of the operation treatment for the nystagmus.

In certain embodiments, the device for testing imaging quality for a nystagmus patient can be implemented by a form of functional units. The unit herein can refer to an ASIC (Application Specific Integrated Circuit), a processor or memory executing one or more software or firmware programs, and/or other devices which can provide the above function(s).

Figure 3:
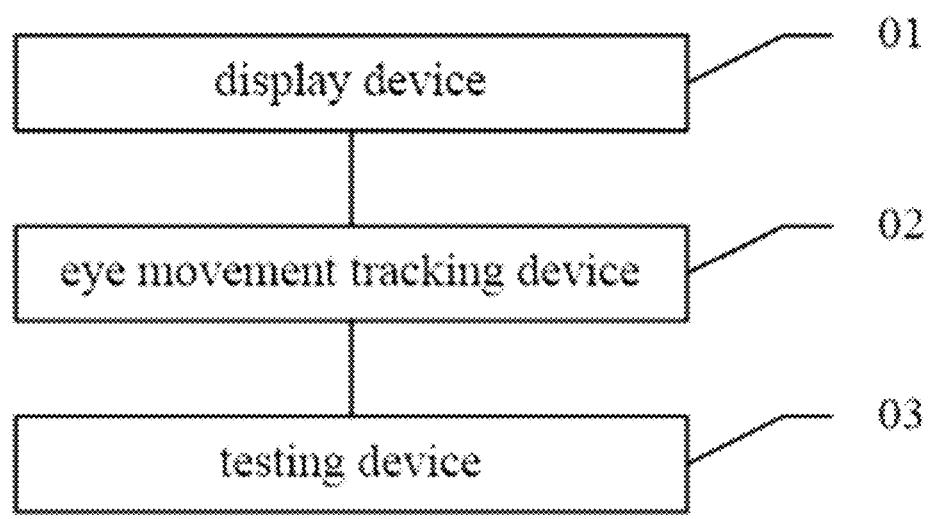
FIG. 3 is structural diagram of an apparatus for testing imaging quality for an eyeball of a nystagmus patient according to an exemplary embodiment of the present disclosure.

In certain embodiments, an apparatus for testing imaging quality for a nystagmus patient is further provided, and as shown in FIG. 3, it comprises: a display device 01, for displaying a visual target; an eye movement tracking device 02, for tracking movement of an eyeball of the nystagmus patient in real time to obtain movement data; and a testing device 03, for adjusting a position of a visual target according to the movement data such that the adjusted position of the visual target is consistent with a sight direction in the movement data; evaluating the imaging quality for the nystagmus patient, according to a vision imaging result when the sight direction is consistent with the position of the visual target, to obtain an evaluation result; and predicting a treatment result of the nystagmus patient according to the evaluation result and a pre-trained treatment evaluation model.

In certain embodiments, the display device 01 can be a display screen, such as an LED screen or an LCD screen, or the like. In certain embodiments, the display device 01 can be selected as an arc shaped screen, which can have a circular center located in the position of the eyeball and a radius larger than 33 cm. In certain embodiments, the, the display screen is designed as the arc shaped screen having a radius larger than 33 cm, so as to provide a wider visual field for the patient to thus make the display more natural, reduce the visual distortion, and improve the comfort of the nystagmus patient in use. In certain embodiments, the display device 01 is formed by combining a plurality of sub-screens. In certain embodiments, the sub-screens can use a design having a narrow frame, and the consistency in brightness and color between the sub-screens is ensured by image calibration. In certain embodiments, the design having the narrow frame can ensure seamless connection of the combined screen. Moreover, the consistency in brightness and color between the sub-screens is ensured by image calibration such that any incoherence and color difference of the image frame can be avoided.

In certain embodiments, the eye movement tracking device 02 can be a device having a high sampling rate, which can be higher than 500 Hz, such as an eye movement tracker. In certain embodiments, in order to capture the fast movement of the nystagmus, a device having a high sampling rate (which can be higher than 500 Hz) is selected to ensure the measurement precision. In addition, the stability is affected by various factors, such as the production quality of the device, the environment factors, the movement of the head to be tested, and so on. Therefore, it is necessary to ensure high stability of the eye movement tracking device 02, thus facilitating reduction in measurement error.

In certain embodiments, a computer apparatus is further provided, comprising the device for testing imaging quality for a nystagmus patient shown in FIG. 2 as described above.

Figure 4:
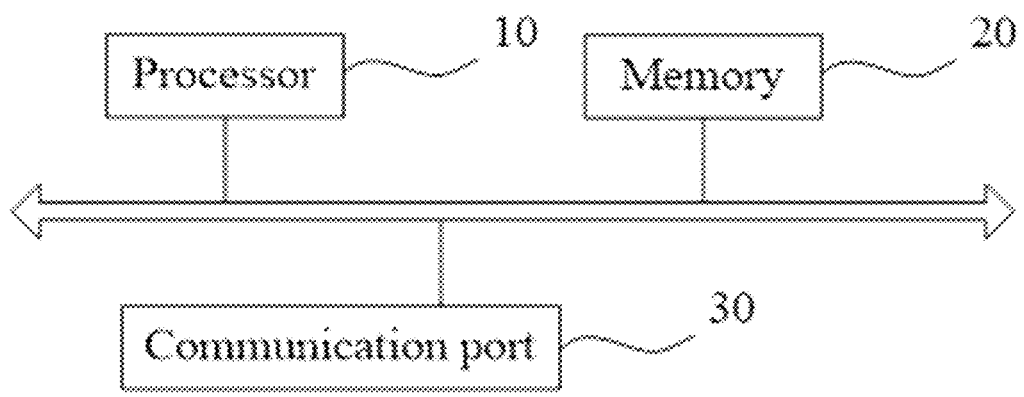
FIG. 4 is a diagram of hardware structure of a computer apparatus of an exemplary embodiment of the present disclosure.

FIG. 4 is a structural diagram of a computer apparatus as provided in an exemplary embodiment of the present disclosure. As shown in FIG. 4, the computer apparatus comprises one or more processors 10, a memory 20, and ports for connecting various components, such as a high-speed port and a low-speed port. The various components are in communication connection with one another by different buses, and can be mounted on a common motherboard or be mounted in other manners as needed. The processor can process instructions executed within the computer apparatus, comprising instructions in a form of graphic information stored in or on the memory to display a GUI on an external input/output device (such as a display apparatus coupled to the port). In certain embodiments, a plurality of processors and/or a plurality of buses and a plurality of memories can be used together. Similarly, in certain embodiments, a plurality of computer apparatuses can be connected, with each providing the necessary operation(s) (which can be used as a server array, a group of blade servers, or a multi-processor system, for example). In FIG. 4, one processor 10 is show as an example.

The processor 10 can be a CPU, a network processor, or a combination thereof. In certain embodiments, the processor 10 can further comprise a hardware chip. In certain embodiments, the above hardware chip can be an ASIC, a PLD, or a combination thereof. In certain embodiments, the above PLD can be a CPLD, a FPGA, a GAL, or any combination thereof.

In certain embodiments, the memory 20 stores an instruction, which can be executed by the at least one processor 10 such that the at least one processor 10 can execute and implement the method(s) as illustrated in the above embodiments.

In certain embodiments, the memory 20 can comprise a storing program region and a storing data region, wherein the storing program region can store an operation system and an application program necessary for at least one function, and the storing data region can store the data created according to the use(s) of the computer apparatus. In addition, in certain embodiments, the memory 20 can comprise a high-speed RAM, and can comprise a non-transient memory, such as at least disk storing device, a flash memory device, or other non-transient solid state storing devices. In certain embodiments, the memory 20 optionally comprises a memory provided remote from the processor 10. Such remote memory can be connected via the network with the computer apparatus. Examples of the above network comprise, but not limited to, the internet, an enterprise intranet, a local area network, a mobile communication network, and a combination thereof.

In certain embodiments, the memory 20 can comprise a volatile memory, such as an RAM. In certain embodiments, the memory 20 can comprise a non-volatile memory, such as a flash memory, a hard disk, a solid-state hard disk. In certain embodiments, the memory 20 can comprise a combination of the above types of memories.

In certain embodiments, the computer apparatus can further comprise a communication port 30, for communication or network communication between the computer apparatus and other apparatuses.

In certain embodiments, a computer-readable storage medium is further provided. The presently disclosed methods can be implemented in the hardware or the firmware, or can be recorded in the storage medium, or can be implemented as computer codes, which are originally stored in a remote storage medium or a non-transient machine-readable storage medium and are downloaded via a network and then stored in a local storage medium, such that the methods can be processed by the soft stored on the storage medium using a general computer, a special processor or a programmable or special hardware. In certain embodiments, the storage medium can be a disk, a CD, a read-only memory, a RAM, a flash memory, a hard disk, or a solid-state hard disk, and so on. In certain embodiments, the storage medium can comprise a combination of the above types of memories/storages. In certain embodiments, a computer, a processor, a micro-processor controller, or a programmable hardware comprises a storing member, which can store or receive the softs or the computer codes. When the softs or the computer codes are accessed and executed by the computer, the processor, or the hardware, the presently disclosed are implemented.

Though exemplary embodiments of the present disclosure are described herein in combination with the figures, various modifications and variations can be made by those skilled in the art without departing from the spirit and scope of the present disclosure. Such modifications and variations are within the scope of the present disclosure.

What is claimed is:

1. A method for testing imaging quality for a nystagmus patient comprising:
    obtaining preoperative movement data of an eyeball of a nystagmus patient in real time;
    adjusting a position of a visual target according to the preoperative movement data such that the adjusted position of the visual target is consistent with a sight direction in the preoperative movement data;
    evaluating the imaging quality for the nystagmus patient, according to a vision imaging result when the sight direction is consistent with the position of the visual target, to obtain an evaluation result; and
    predicting a postoperative result of the nystagmus patient according to the evaluation result and a pre-trained treatment evaluation model,
    wherein the movement data comprises one or more information related to eyeball movement selected from the group consisting of a position of the eyeball, a movement speed of the eyeball, and the eyeball movement track.

2. The method of claim 1, wherein the step of adjusting the position of the visual target according to the preoperative movement data comprises:
    obtaining preoperative historical movement data of the eyeball of the nystagmus patient;
    using the historical movement data to build an eye movement prediction model configured to predict movement data of the eyeball;
    predicting movement data of the eyeball at the next moment according to the eye movement prediction model and the movement data of the eyeball at the current moment; and
    adjusting the position of the visual target according to the sight direction determined by the predicted movement data of the eyeball at the next moment,
    wherein the historical movement data comprise one or more information related to eyeball movement selected from the group consisting of a position of the eyeball, a movement speed of the eyeball, and the eyeball movement track.

3. The method of claim 2, wherein the step of using the historical movement data to build the eye movement prediction model comprises:
    performing fitting analysis for the historical movement data based on the anatomical and physiological principles to build the eye movement prediction model; or
    using the historical movement data to train an autoencoder to build the eye movement prediction model.

4. The method of claim 3, wherein after the step of obtaining the preoperative movement data of the eyeball of the nystagmus patient in real time, the method further comprises performing filtering processing to the preoperative movement data.

5. The method of claim 3, wherein the step of predicting the postoperative result of the nystagmus patient according to the evaluation result and the pre-trained treatment evaluation model comprises:
    obtaining a historical evaluation result of the eyeball of the nystagmus patient and a corresponding treatment result;
    using the historical evaluation result and the corresponding treatment result to to obtain the treatment evaluation model; and
    inputting the evaluation result into the treatment evaluation model to determine the postoperative result of the nystagmus patient.

6. The method of claim 2, wherein the historical movement data is obtained using an eye movement tracking device.

7. The method of claim 1, wherein the step of adjusting the position of the visual target according to the preoperative movement data comprises:
    a) obtaining preoperative historical movement data of the eyeball of the nystagmus patient;
    b) using the historical movement data to build a nystagmus identification model for identifying a speed and an amplitude of the nystagmus;
    c) inputting the movement data of the eyeball as obtained in real time into the nystagmus identification model to identify the current speed and amplitude of the nystagmus; and
    d) adjusting the position of the visual target according to the current speed and amplitude of the nystagmus.

8. The method of claim 7, wherein the historical movement data is obtained using an eye movement tracking device.

9. The method of claim 1, wherein after the step of obtaining the preoperative movement data of the eyeball of the nystagmus patient in real time, the method further comprises performing filtering processing to the preoperative movement data.

10. The method of claim 1, wherein the step of predicting the postoperative result of the nystagmus patient according to the evaluation result and the pre-trained treatment evaluation model comprises:
    obtaining a historical evaluation result of the eyeball of the nystagmus patient and a corresponding treatment result;
    using the historical evaluation result and the corresponding treatment result to obtain the treatment evaluation model; and
    inputting the evaluation result into the treatment evaluation model to determine the postoperative result of the nystagmus patient.

11. The method of claim 1, wherein the evaluation result comprises visual clarity, contrast, and stability.

12. A computer apparatus comprising a memory and a processor, wherein the memory and the processor are in communication with each other, wherein a computer instruction is stored on the memory, and when the computer instruction is executed by the processor, the method for testing imaging quality for the nystagmus patient according to claim 1 is implemented.

13. A computer-readable storage medium comprising a computer instruction stored therein, wherein the computer instruction is used to enable a computer to implement the method for testing imaging quality for the nystagmus patient according to claim 1.

14. The method of claim 1, wherein the preoperative movement data is obtained using an eye movement tracking device.

15. A device for testing imaging quality for a nystagmus patient, comprising:
- a data obtaining module, for obtaining preoperative movement data of an eyeball of a nystagmus patient in real time;
- an adjusting module, for adjusting a position of a visual target according to the preoperative movement data such that the adjusted position of the visual target is consistent with a sight direction in the preoperative movement data;
- an evaluation module, for evaluating the imaging quality for the nystagmus patient, according to a vision imaging result when the sight direction is consistent with the position of the visual target, to obtain an evaluation result; and
- a prediction module, for predicting a treatment result of the nystagmus patient according to the evaluation result and a pre-trained treatment evaluation model,
- wherein the movement data comprises one or more information related to eyeball movement selected from the group consisting of a position of the eyeball, a movement speed of the eyeball, and the eyeball movement track.

16. The device of claim 15, wherein adjusting the position of the visual target according to the preoperative movement data comprises:
- obtaining preoperative historical movement data of the eyeball of the nystagmus patient;
- using the historical movement data to build an eye movement prediction model configured to predict movement data of the eyeball;
- predicting movement data of the eyeball at the next moment according to the eye movement prediction model and the movement data of the eyeball at the current moment; and
- adjusting the position of the visual target according to the sight direction determined by the movement data of the eyeball at the next moment,
- wherein the movement data comprises one or more information related to eyeball movement selected from the group consisting of a position of the eyeball, a movement speed of the eyeball, and the eyeball movement track.

17. The device of claim 16, wherein using the historical movement data to build the eye movement prediction model comprises:
- performing fitting analysis for the historical movement data based on the anatomical and physiological principles to build the eye movement prediction model; or
- using the historical movement data to train an autoencoder to build the eye movement prediction model.

18. The device of claim 17, further comprising a filtration module, for performing filtering processing to the preoperative movement data.

19. The device of claim 17, wherein predicting the postoperative result of the nystagmus patient according to the evaluation result and the pre-trained treatment evaluation model comprises:
- obtaining a historical evaluation result of the eyeball of the nystagmus patient and a corresponding treatment result;
- using the historical evaluation result and the corresponding treatment result to obtain the treatment evaluation model; and
- inputting the evaluation result into the treatment evaluation model to determine the postoperative result of the nystagmus patient.

20. The device of claim 16, wherein the historical movement data is obtained using an eye movement tracking device.

21. The device of claim 15, wherein adjusting the position of the visual target according to the preoperative movement data comprises:
- obtaining preoperative historical movement data of the eyeball of the nystagmus patient;
- using the historical movement data to build a nystagmus identification model for identifying a speed and an amplitude of the nystagmus;
- inputting the movement data of the eyeball as obtained in real time into the nystagmus identification model to identify the current speed and amplitude of the nystagmus; and
- adjusting the position of the visual target according to the current speed and amplitude of the nystagmus,
- wherein the movement data comprises one or more information related to eyeball movement selected from the group consisting of a position of the eyeball, a movement speed of the eyeball, and the eyeball movement track.

22. The device of claim 21, wherein the historical movement data is obtained using a testing device.

23. The device of claim 15, further comprising a filtration module, for performing filtering processing to the preoperative movement data.

24. The device of claim 15, wherein predicting the postoperative result of the nystagmus patient according to the evaluation result and the pre-trained treatment evaluation model comprises:
- obtaining a historical evaluation result of the eyeball of the nystagmus patient and a corresponding treatment result;
- using the historical evaluation result and the corresponding treatment result to obtain the treatment evaluation model; and
- inputting the evaluation result into the treatment evaluation model to determine the postoperative result of the nystagmus patient.

25. The device of claim 15, wherein the evaluation result comprises visual clarity, contrast, and stability.

26. The device of claim 15, wherein the preoperative movement data is obtained using an eye movement tracking device.

* * * * *